United States Patent [19]

Alexander et al.

[11] Patent Number: 5,679,231
[45] Date of Patent: Oct. 21, 1997

[54] GEL BED DIALYZER

[76] Inventors: Donald H. Alexander, 212 High Meadows, Richland, Wash. 99352; Nabil Morcos, P.O. Box 50922, Idaho Falls, Id. 83405

[21] Appl. No.: 388,208

[22] Filed: Feb. 13, 1995

[51] Int. Cl.$^6$ .................................................. B01D 61/30
[52] U.S. Cl. ................ 204/627; 210/321.6; 210/321.64; 210/321.87; 210/321.88
[58] Field of Search ................... 204/182.3, 182.4, 204/182.5, 182.6, 301, 627; 210/321.6, 321.64, 321.87, 321.88

[56] References Cited

U.S. PATENT DOCUMENTS 4,075,108  2/1978  Higley et al. ................. 210/500 M
4,306,556  12/1981  Zelman ......................... 128/272
4,308,145  12/1981  Higley et al. ................. 210/646
5,208,156  5/1993  Shibatani et al. .............. 435/196

Primary Examiner—Arun S. Phasge
Attorney, Agent, or Firm—Donald H. Alexander; Nabil Morcos

[57] ABSTRACT

A hemodialysis apparatus separates constituents from blood plasma utilizing layered gel membranes of differing permeabilities configured as a U-tube. Physical filter pressing of blood plasma is accomplished by pinching gel beds along the U-tube axis where localized pressure rise and centrifugal forces are established. The U-tube fold also establishes chemical countercurrent pumping across the gel beds. Capillary and electroosmotic gel filtration further accomplishes selective chemical removal and readsorption.

1 Claim, 4 Drawing Sheets

GEL BED DIALYZER

BACKGROUND OF THE INVENTION

Dialysis is the process of separating substances from solution by means of their unequal diffusion through semi-permeable membranes. Differences in pressure and osmotic potential across the walls of a capillary or semi-permeable membrane are responsible for the exchanges of gases, solutes, dissolved substances, microparticulates, and colloids.

Prior Art

Hemodialysis is a mechanical-chemical application for the removal of unwanted impurities and fluids which accumulate in the blood as a consequence of kidney failure. Basically, dialytic systems or machines of concern effect separation of crystalloids from colloids in solution by diffusion and ultrafiltration of the crystalloids through a moistened membrane. The above is accomplished by passing the blood or body fluids of the patient under treatment through an artificial kidney. Such a device includes a moistened membrane, across one surface of which blood is circulated, and along the other surface of which a dialysis solution is circulated. The dialysis solution consists of dissolved salts, especially formulated to approximate the sought-after and desired chemical makeup of the blood to be treated. As a result of dialysis, the chemical makeup of the blood flowing across one surface of the membrane is converted or altered during treatment, until it is balanced with the chemical makeup of the dialysis solution.

The in vitro artificial kidney is applied to patients with end stage renal diseases and is used for the treatment of certain heart conditions, scleroderma, removal of metabolites from methyl alcohol poisoning, chronic peritonitis, and other applications.

An artificial kidney is currently available in a variety of types such as a coil dialyzer (Kolf Twin Coil), Kiil or parallel flow dialyzer, and capillary or hollow fiber dialyzer. These types of artificial kidneys have different constructions, but share common features. They consist primarily of two chambers partitioned by a semi-permeable monolayer membrane. One chamber, a blood chamber, contains the blood to be dialyzed. The other chamber, a dialysate chamber, contains the flow of dialysate. In these prior art methods the blood pressure flowing through the blood chamber must be higher than that of the dialysate flowing through the dialysate chamber in order to remove excess water and impurities from the patient's blood.

Coil kidney dialyzers (Kolf) are often used in single pass-recirculating mode or systems which require high dialysate flow rates through the system; for example, in excess of 15 liters per minute. No control is necessary over the dialysate pressure in such an apparatus since the dialyzer is open to atmospheric pressure. In the second type of artificial kidney dialyzer, capillary or parallel flow membranes are provided. In single pass dialyzers, the dialysate flows directly through parallel paths in a single pass about the membranes with no recirculation of the dialysate. Flow rates of from 100 cc to 1 liter per minute are often used. However, the required dialysate flow rate through the dialysate chamber to perform an effective hemodialysis varies with the type of dialyzer. Such systems are closed to the atmosphere and pressure control of the dialysate in the dialyzer is used to provide the necessary pressure and flow.

In a coil dialyzer, blood is pumped under pressure through the blood chamber while dialysate is pumped through the dialysate chamber under a pressure equal or approximate to atmospheric pressure. The pressure differential required to diffuse metabolic waste products from the blood through the semi-permeable membrane into the dialysate chamber varies with the type of dialyzer.

The Kiil dialyzer consists of a pair of sheet-like membranes with opposing inner surfaces, between which the blood being treated is circulated. The sheets are arranged between a pair of plate-like members with opposing dialysate conducting channels. Opposing flow of dialysate sets up a countercurrent. Dialysate is circulated through the channels under a controlled pressure which is less than that of the blood under treatment. This pressure differential draws the membranes, to a predetermined extent, into the channels in the plates and defines blood conducting channels in and between the sheets. The negative pressure imposed upon the dialysate controls the rate of dialysis. The blood passes over a semi-permeable membrane and through thousands of hollow permeable fibers which are immersed in a dialysate solution. The impurities pass through the capillary fibers into the dialysate solution by diffusion. Excess fluid in the blood diffuses into the dialysate solution due to a difference in pressure across the membrane. The latter process is referred to as ultrafiltration. Where a Kiil or capillary or hollow fiber dialyzer is utilized, the blood to be dialyzed is allowed to flow under its own pressure through the blood chamber while the dialysate is pumped through the dialysate chamber under a pressure lower than the blood pressure.

Numerous efforts have also focused on the development of an artificial liver. A number of workers have applied dialysis in a manner similar to the artificial kidney discussed above. Some have used suspended hepatocyte gel beads. None have used the gel bed filtration techniques of this invention.

The primary object of this application is to provide a more efficient and more compact alternative to prior art dialyzers which make use of hollow fiber capillaries or monolayer membranes for applications from hemodialysis to chemical separations.

The electroosmotic gel bed dialyzer, referred to hereafter as the "gel bed dialyzer" is an apparatus for the extraction of a wide range of substances from aqueous based solutions such as blood plasma on the basis of physical and chemical mechanisms established by a U-tube configured set of planar gel beds.

The U-tube geometry is a critical feature of the invention since it establishes radial filter pressing and countercurrent pumping. Physical filter pressing of blood plasma is accomplished by pinching gel beds along the U-tube axis accomplishing localized pressure rise and centrifugal forces.

The U-tube fold further establishes chemical countercurrent pumping across the gel beds between adjacent limbs, analogous to countercurrents in the Loop of Henle in the natural kidney. Capillary and electroosmotic forces within the dialyzer further accomplishes selective chemical removal and readsorption.

In simplest embodiment, the gel bed dialyzer is designed such that laminar blood flow occurs in a planar layer between strategically stratified gel bed membranes. The layered, planar gel bed membranes are folded along a mid-plane axis in a U-tube configuration which comprises the blood chamber. The gel bed membranes are bathed in a dialysate solution. The dialysate fluid passes through two enclosing chambers, one above and one below the blood chamber. The dialysate in the enclosing chambers is directed in opposing directions to take advantage of accelerated diffusion due to chemical potential gradients established by the countercurrent.

ELECTROOSMOTIC GEL FILTRATION

Several immediate advantages are realized with this invention. The gel bed exerts stronger and more uniform capillary forces than in prior art technologies. In essence, the pathways among and through the beads in the gel bed can be visualized as a network of micro-capillaries. The micro-capillary fringe dramatically increases filtration efficiency compared to hollow fiber devices because of the significant increase in surface to volume ratio, i.e., the effective number of capillaries per unit volume is dramatically increased. Monolayer membranes exert no capillary forces. Second, the diffusion of species across the gel bed membranes is enhanced by radial filter pressing in the U-tube configuration. Finally, specialized separations can be practiced within the invention by changing bead size and selecting from a variety of gel compositions used in pre-existing art including affinity chromatography, ion exchange, and electrophoresis.

SUMMARY OF THE INVENTION

The primary objective of this invention is to accomplish extractions by passively exerting mechanical, chemical, and electromotive pressures for withdrawal of ultrafiltrate and reducing reliance on mechanical methods or eliminate them altogether.

A further objective of this invention is to provide a means of selectively extracting substances from aqueous liquids such as blood plasma in a highly compact device.

The foregoing objectives are achieved in accordance with the present invention by incorporating gel bed membranes into a planar "U-tube pump" configuration to accomplish dialysis. The substances are extracted through contained gel beds which serve collectively as an ultrafiltration device that can be chemically selective. The gel beds perform as layered semi-permeable membranes which also exert their own capillary pressure and may be made to be chemically selective. The capillary capacity of the gel bed design is much greater than that of prior art capillaries because of the substantial increase in surface area per occupied volume. Prior art capillaries are designed as hollow fibers with fixed apertures. The instant invention establishes capillaries with diameters defined by the aperture or pore diameter of passage ways between beads in the gel bed. This is a critical feature of the invention: the aperture diameter of the pores is adjustable in the gel bed dialyzer.

Accelerated migration of substances across the gel bed is accomplished by applying an electromotive force. The gel properties are selected on the basis of requirements for pore size, permeability, operating conditions in the solute (e.g., pH, temperature, composition) and affinity for scavenging specific substances (binding capacity). Typically, gels are selected which permit minimal (inert where possible) interaction with the phase(s) being separated in dialysis applications; i.e., where substances are physically separated on the basis of aperture and pore diameter among beads. Substances separated in this manner may be subjected to further separation steps.

This invention eliminates the need for semi-permeable membranes and capillary tubes by substituting gels in their place. Gels act as semi-permeable membranes and simultaneously exert a high capacity capillary force by the imbibition of liquids. The method further utilizes electroosmotic pumping and reduces reliance on mechanical pumps, valves, and connecting tubes routinely used in capillary dialysis.

DESCRIPTIONS OF THE DRAWINGS

These and other objects of the present invention will become readily apparent from the following description taken in conjunction with preferred embodiments thereof, with reference to the accompanying drawings in which:

FIG. 1 preferred embodiment of the artificial kidney gel bed dialyzer.

FIG. 2 cross-section, planar, and right lobe perspectives of gel bed dialyzer.

FIG. 3 portable electroosmotic gel bed dialyzer.

DETAILED DESCRIPTION OF THE PREFERRED EMBODIMENT

Figure 1:
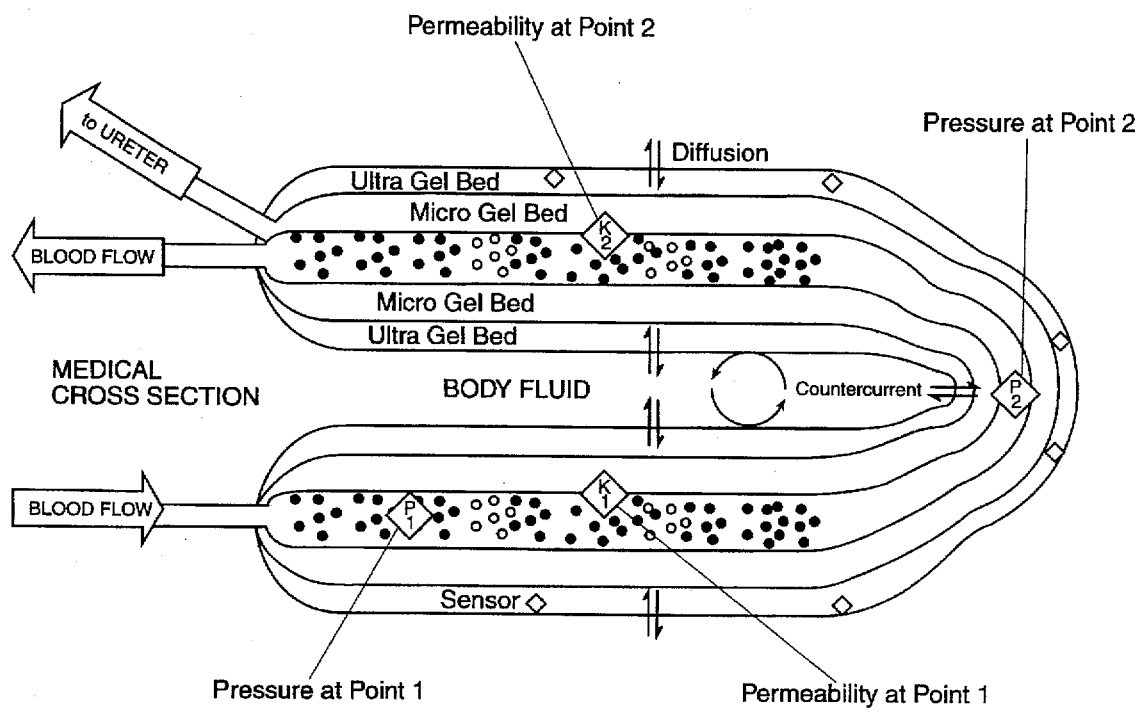

The preferred embodiment of the electroosmotic gel bed dialyzer is provided in FIG. 1. The dialyzer comprises micro and ultra gel beds which encase a blood flow through chamber, which beds are arranged as a U-tube with inlet and outlet ports to allow flushing of individual beds and replacement of gel beads. The gel bed layers and blood chamber are decreased in aperture or "pinched" at the hinge of the U-tube. The dialyzer may be fitted with sensors or electrodes as indicated. The dialyzer makes use of gel beads which comprise silicates, aluminates, titanates, zirconates, vanadates, other amorphous gels, and organic-based gel beads. As in the prior art, blood pressure may be established directly by the heart or enhanced with a mechanical pump assist.

The preferred embodiment relies on the control of fluid flow characteristics resulting from the geometry of the device to facilitate physical separation of the target substances from the raw process streams. Radial filter pressing, due to the centrifugal force along the fold axis, forces the separable constituents to pass through the gel beds according to size. The constriction in the flow path at the hinge axis results in a local rise in blood pressure. Blood pressure drives the system and results in a countercurrent ion pump as a result of the hinge fold axis of the enclosing gel bed membranes.

The central layer, or blood chamber, channels the flow of fluid, in this case blood, between four semi-permeable membranes. Membrane porosity and permeability is selected so that blood component substances such as red or white corpuscles, proteins or other large molecular weight solids cannot pass through the enclosing gel bed membranes and therefore continue in the indicated direction of flow.

Micro gel bed membrane porosity and permeability is larger than the dimensions of the substances to be separated such as urea, uric acid, dissolved ions ($Na^+$, $Cl^-$, $K^+$ and $NH^4+$) and water allowing these substances to pass out of the blood. The porosity and permeability is controlled by the selection of bead diameter. The beads establish intrabead and interbead pores. Capillary forces draw water along with entrained and dissolved substances through the pores.

Several gel bed layers may be utilized to enable multiple levels of separation. In FIG. 1, the micro gel layer allows the separation of urea, uric acid, microparticulates, colloids, water and dissolved ions ($Na^+$, $Cl^-$, $K^+$ and $NH^4+$). Only water and dissolved ions pass into an ultra gel bed filter with reduced porosity and permeability and come in contact with the dialysate.

Strategically engineered membrane permeability is an important aspect of the gel bed dialyzer. Specifically, the membrane permeability at K1 in FIG. 1 is designed to be greater than that of the membrane at point K2. Permeability at point K1 allows diffusion of urea, crystalloids, water, and other electrolytes from the incoming blood to pass into the micro gel bed. The permeability at point K2 excludes urea and uric acid from passing back into the blood stream by design. The permeability at K2 is designed to allow osmotic resorption of water from the effluent stream back into the blood stream. The gel bed membrane apertures at K1 are greater than urea whereas the gel bed membrane apertures at K2 are less than urea but are sufficient to allow water to be resorbed by the blood. This is an important feature of the gel bed dialyzer, since prior art dialyzers are not designed to directly resorb water to the blood.

The preferred embodiment also comprises the ability to backflush the gel bed. This is an important aspect of the invention because, under a range of conditions the gel beds will clog with extended use. Backflushing of the gel bed is accomplished by manual flushing or alternatively by reversing the polarity of the electromotive force normal or at an acute angle to the longitudinal axis of the gel bed (i.e., perpendicular to the plane of the gel bed).

Countercurrent gradients typical of the Loop of Henle in the natural kidney can be further engineered by properly distributing the micro-electrodes along the longitudinal axis of the gel beds (indicated by diamonds in FIG. 1). One method to augment the countercurrent ion pump is to increase the electromotive driving force (or current) along the longitudinal axis of process stream flow. Alternatively, the design promotes initiation of ion cross current gradients by causing the dialysate to flow in opposing directions above and below the outer membranes. This effect is further enhanced by adjusting the permeability along the longitudinal axis, to create an osmotic gradient or by creating a chromatographic affinity gradient. Selective separation and extraction of various substances can be accomplished through the use of affinity chromatography. For example, glucose can be selectively absorbed and released from a designated membrane. This is also an important aspect of the invention.

The preferred embodiment also comprises sensors such as fiber optrodes (also indicated by diamonds in FIG. 1) which can be inserted into the membranes to allow remote monitoring of fluid chemistry (pH, composition, alkalinity) and conditions (temperature and pressure).

Figure 2A:
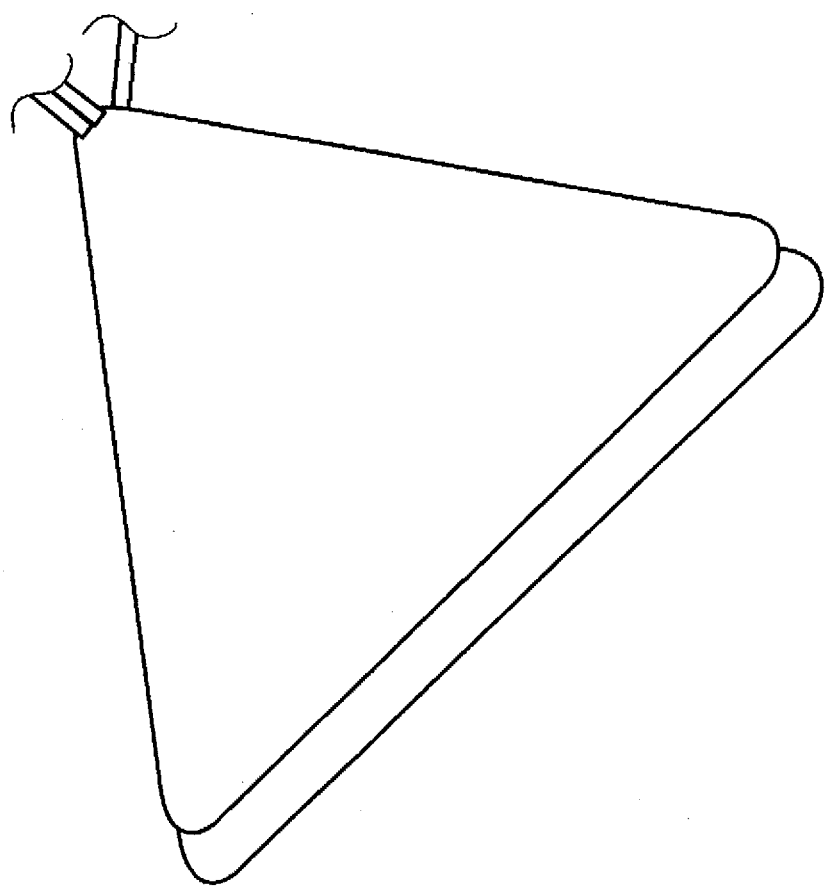
Figure 2B:
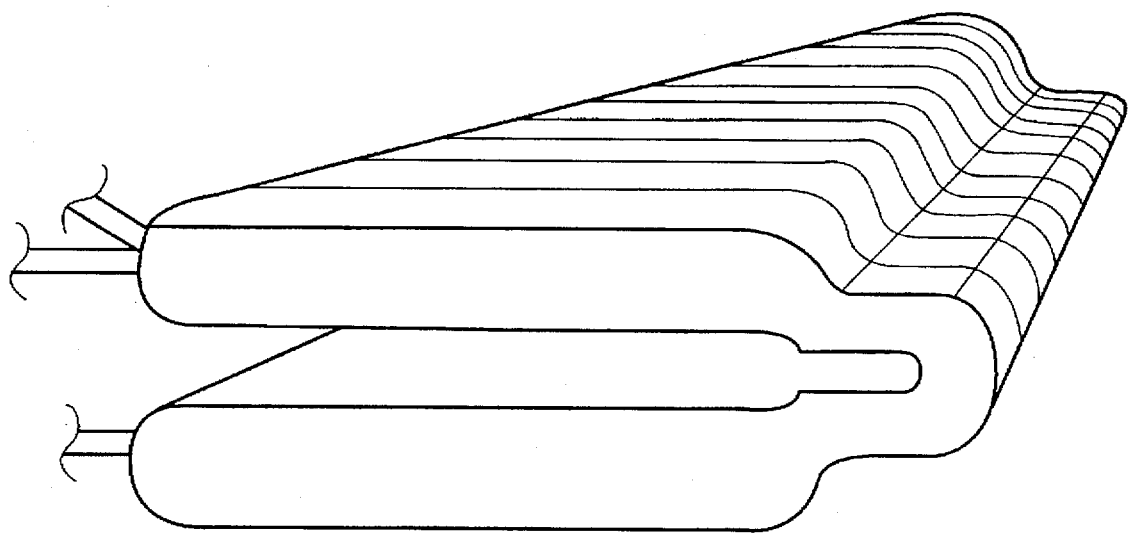

FIG. 2 shows a longitudinal section through the in vivo artificial kidney. The system is folded at the midpoint of the longitudinal axis to take advantage of the centrifugal filter pressing and countercurrent pump effect of the natural kidney (Loop of Henle). In addition to the fold, the gel bed dialyzer enhances the countercurrent by pinching the flow pathways along the axis of the hinge. These two attributes create a pressure gradient and increase flow rate along the restricted path (shown as P2 in the figure). The countercurrent is caused by the unequal concentrations of $Na^+$ in the limbs of the gel bed dialyzer. Existing technological breakthroughs in the miniaturization of microprocessor chips, sensors, and electrical energy sources applied in the development of the artificial heart can be coupled with the invention. Design views of the artificial kidney including planar (top), right lobe perspective, and cross-section are provided in FIG. 2.

Gel Bed Design

The gel bed dialyzer utilizes of a set of gel bed filters in a molecular micro-sieve arrangement. Prior art gels can shrink or swell in response to osmotic pressure. This invention incorporates these gels into fixed beds and applies the property to regulate gel bed membrane permeability. Progressive osmotic gel bead shrinking or swelling between fixed membranes is controlled in confined beds. This process is accomplished by controlling the chemical concentration gradient within and external to the gel bed membrane.

Gel beds are designed such that the amorphous gels or porous gel beads are encased by fixed membranes. A wide range of amorphous and porous bead gels are available for use in the application and are widely in use for affinity chromatography, ion exchange, and electrophoresis. Several suppliers such as SUPELCO, Bellafonte Park, Pa. offer tailored gels for physical separations based on size ranging from less than 125 angstroms to greater than 4000 angstroms. The substitution of the gels for capillary-based transport mechanisms in the gel bed dialyzer increases the number of path-ways per cross-sectional area and allows smaller scale devices than prior art capillary units.

The invention also accommodates gel bed bioreactor technology which allows "metabolic-like" reactions typical of epithelial membranes by the incorporation of gel bead bioreactors (or microcarriers) into the gel bed or synthetic epithelium. By ordering the synthetic epithelial tissue in a strategic stratigraphic arrangement complex "metabolic-like" reactions can be realized.

This is a necessary advance for the in vivo applications of the invention. Each bed contains beads with a specific molecule(s) and/or salt(s). These beads become the site of reactions with ions carried by in-coming solutions. The reactions within each gel bed or synthetic epithelium produces a by-product compound which is released from the bed for further reactions with the products of adjacent beds. Thus a series of simultaneous reactions occur simulating, e.g., metabolism in living organisms.

Microcarrier gel beads enclosing reactive hepatocytes are optionally incorporated in a gel bed epithelium which serves as a hepatocyte bioreactor. The hepatocytes are cultured from the human liver and incorporated in the gel beads as in the prior art. These beads are then incorporated in the synthetic epithelium of this invention. The device is designed so that each synthetic epithelial membrane can be recharged with gel bead microcarriers as required to maintain desired reaction rates.

Figure 3:
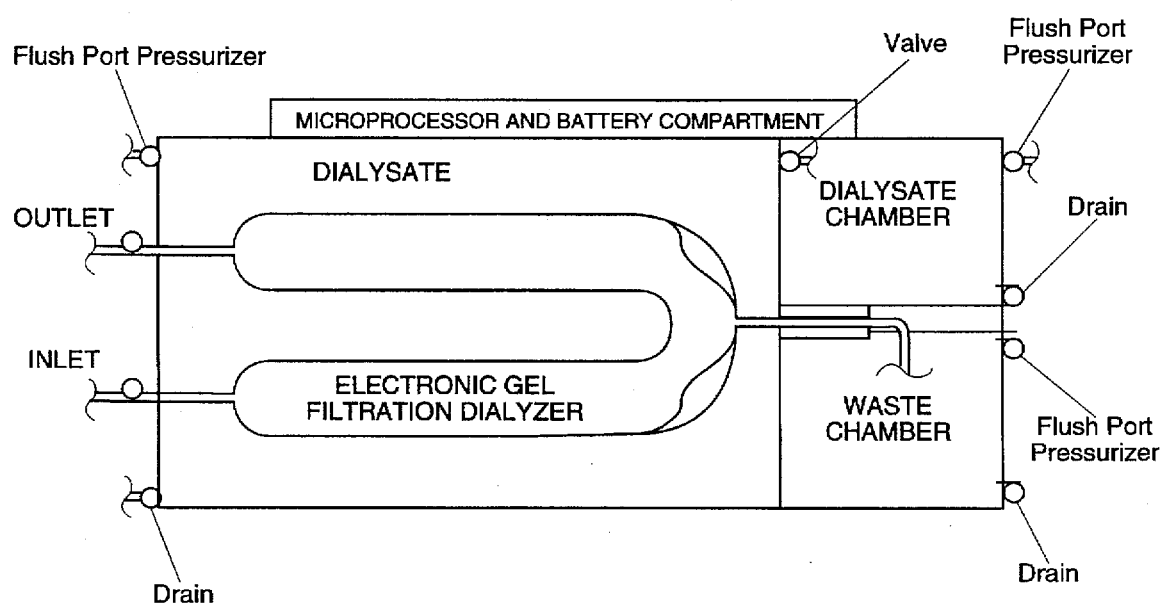

This embodiment also comprises the temporary operation without drainage, of a device similar to that shown in FIG. 2. Processed wastes in the portable unit are sent to a waste chamber. A portable electroosmotic gel filtration dialysis unit is illustrated in FIG. 3.

EXAMPLES

The following examples are illustrative of the present invention:

EXAMPLE 1

Removal of Contaminants from Bodily Fluids

Urea, uric acid, and other nitrogenous wastes, glucose, excess water, salts, crystalloids, metals and other toxins, ammonia, and bacteria and viruses are substances which can be removed from the blood by the application of the present invention. As an example, extractions of urea through a gel were conducted. The urea was drawn through the gel by an electromotive force. The measurements of the urea extractions were taken over time to monitor the rate of urea recovery and the interaction with the gel.

Experimental method

A two centimeter thick plug of aluminum hydroxide—ethylene diamine tetraacetic acid (EDTA) gel complex was placed in the axis of a U tube encased on each side with glass frits. A 1% solution of urea was prepared in distilled deionized water. It was slightly acidified to produce $CO(NH_3)_2^{2+}$ and placed in the right hand side of the U tube. An equal volume of normal saline solution was placed in the left arm of the U tube. A cathode was placed at the saline side arm of the tube to attract cations. The corresponding anode was placed at the urea-containing side arm of the tube. A potential of 3.0 volts was maintained between the electrodes at 800 mA. Five hundred microliters samples were extracted from the saline side arm of the tube at 0.0, 5.0, 15.0, 30.0, 60.0, 120.0, and 240.0 minute intervals and analyzed for urea concentration. The results are summarized in Table 1.

TABLE 1

Urea Separation with Gel Membrane

| Time (min.) | Urea Concentration (mg/L) |
|---|---|
| 0 | 0 |
| 5 | 155.0 |
| 15 | 280.0 |
| 30 | 410.0 |
| 60 | 560.0 |
| 120 | 770.0 |
| 240 | 1000.0 |

The data in Table 1 shows that urea is transported through the gel under an electromotive force with a useable and practical rate.

EXAMPLE 2

Medical and Pharmaceutical Separations

Numerous substances are extracted from various process streams for use as pharmaceuticals such as vitamins, steroids, antibiotics, and analgesics. Medical researchers separate substances such as bacteria, viruses, proteins, amino acids, high molecular weight organics, cells, coagulation factors, enzymes, lectins, and receptors to name a few. As an example, further experiments were conducted to separate salicylic acid using a gel. The imposition of an electrical current in the separation process was experimentally observed to enhance the separation for salicylic acid.

A two centimeter thick plug of aluminum hydroxide—ethylene diamine tetraacetic acid (EDTA) gel complex was placed in the axis of a U tube encased on each side with glass frits. A solution of salicylic acid (2 g/960 mL or 2080 ppm) was prepared in distilled deionized water and placed in the right hand side of the U tube. An equal volume of normal saline solution was placed in the left arm of the U tube. A cathode was placed at the salicylic acid side arm of the tube. The corresponding anode was placed at the saline side arm of the tube. A potential of 2.8 volts was maintained between the electrodes at 600 mA. Five hundred microliters samples were extracted from the saline side arm of the tube at 0.0, 5.0, 15.0, 30.0, 60.0, 120.0, and 240.0 minute intervals and analyzed for urea concentration. The results are summarized in Table 2.

TABLE 2

Salicylic Acid Separation with Gel Membrane

| Time (min.) | Salicylic Acid Concentration (pp.m or mg/L) |
|---|---|
| 0 | 0 |
| 5 | 85.0 |
| 15 | 178.0 |
| 30 | 325.0 |
| 60 | 540.0 |
| 120 | 927.0 |
| 240 | 1600.0 |

The data in Table 2 shows that salicylic acid is transported through the gel under an electromotive force with a useable and practical rate.

The above experiment was repeated with a saturated salicylic acid solution. The concentrations of salicylic acid in the periodic samples are summarized in Table 3, and are in general agreement with the previous experiment.

TABLE 3

Salicylic Acid Separation with Gel Membrane

| Time (min.) | Salicylic Acid Concentration (ppm or mg/L) |
|---|---|
| 0 | 0 |
| 5 | 230.0 |
| 15 | 510.0 |
| 30 | 1125.0 |
| 60 | 1970.0 |
| 120 | 2780.0 |
| 240 | 5110.0 |

To assess the effect of current flow through the separation scheme, the same experiment was repeated with the exception of reversing the current flow through the U tube. The transfer of salicylic acid towards the saline side arm was greatly depressed as indicated by the results shown in Table 4. This data also shows that the gels can be back flushed by reversing polarity of the driving electromotive force. In addition, the data also show that process of substance transfer through the gels can be controlled by an electromotive force.

TABLE 4

Salicylic Acid Separation with Gel Membrane Under reverse current flow

| Time (min.) | Salicylic Acid Concentration (ppm or mg/L) |
|---|---|
| 0 | 0 |
| 5 | 0 |
| 15 | 17.0 |
| 30 | 23.0 |
| 60 | 57.0 |
| 120 | 71.0 |
| 240 | 132.0 |

Water Purification

Ultrapurification of water can be accomplished with the application of the gel bed dialyzer as described above and illustrated in FIGS. 1–3. Very low concentrations of impurities can be extracted. Typically, aqueous waste streams would first be clarified and purified using conventional filtration techniques. Metals, metal salts, viruses, radionuclides, and organic contaminants can be separated using electroosmotic gel filtration dialysis.

What is claimed is:

1. A gelatinous bed dialyzer apparatus which comprises a flow through fluid processing chamber encased by one or more membranes filled with gelatinous substances which further comprises:
   a. membranes and fluid processing chambers of said device which are folded in U-tube configuration;
   b. the axial fold of said U-tube having a constricted flow cross section as compared to the U-tube limbs to allow radial filter pressing of the dialysate from the feed solution/suspension;
   c. the membranes comprising the limbs of said U-tube are filled with gelatinous material have different permeability and chemical reactivities to establish selective differing chemical speciation and readsorption processes in the adjacent limbs of the apparatus;
   d. the gel-filled chamber membranes establish a chemical counter-current pumping across the gelatinous bed and between the adjacent limbs of the apparatus; and
   e. chemical species countercurrents established in said U-tube by the capillary and electroosmotic forces effect the selective chemical speciation and re-adsorption processes.

* * * * *